(12) United States Patent
Yoon et al.

(10) Patent No.: US 9,151,735 B2
(45) Date of Patent: Oct. 6, 2015

(54) CYANINE DERIVATIVES HAVING MESO-REACTIVE FUNCTIONAL GROUP AT POLYMETHINE CHAIN AND PREPARATION METHOD THEREOF

(71) Applicant: Ewha University-Industry Collaboration Foundation, Seoul (KR)

(72) Inventors: Juyoung Yoon, Seoul (KR); Guo Zhiqian, Seoul (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 13/813,764

(22) PCT Filed: Jan. 7, 2013

(86) PCT No.: PCT/KR2013/000089
§ 371 (c)(1),
(2) Date: Feb. 1, 2013

(87) PCT Pub. No.: WO2013/109011
PCT Pub. Date: Jul. 25, 2013

(65) Prior Publication Data
US 2014/0329331 A1    Nov. 6, 2014

(30) Foreign Application Priority Data
Jan. 20, 2012  (KR) .................. 10-2012-0006796

(51) Int. Cl.
| | | |
|---|---|---|
| *G01N 31/22* | (2006.01) | |
| *G01N 31/00* | (2006.01) | |
| *C07D 403/08* | (2006.01) | |
| *C07D 403/02* | (2006.01) | |
| *C07D 209/14* | (2006.01) | |
| *G01N 33/84* | (2006.01) | |
| *C09B 23/01* | (2006.01) | |

(52) U.S. Cl.
CPC ............ *G01N 31/221* (2013.01); *C07D 209/14* (2013.01); *C07D 403/08* (2013.01); *C09B 23/0041* (2013.01); *C09B 23/0066* (2013.01); *G01N 33/84* (2013.01); *Y10T 436/163333* (2015.01)

(58) Field of Classification Search
CPC ... G01N 31/22; G01N 31/221; G01N 31/224; G01N 27/626; G01N 21/78; C07D 403/08; C07D 403/02; C07D 403/00; Y10T 436/163333; Y10T 436/16; Y10T 436/172307; Y10T 436/17; Y10T 436/00
USPC .......................................... 436/104, 103, 163
See application file for complete search history.

(56) References Cited

U.S. PATENT DOCUMENTS

| 7,172,907 B2 * | 2/2007 | Chen et al. ..................... 436/546 |
| 2004/0132092 A1 * | 7/2004 | Stetson et al. ................. 435/7.1 |
| 2011/0159519 A1 * | 6/2011 | Schmidt et al. ................ 435/7.2 |

FOREIGN PATENT DOCUMENTS

| WO | 2006/072580 A1 | 7/2006 |
| WO | 2011/139275 A1 | 11/2011 |

OTHER PUBLICATIONS

Han, Junyan et al., Fluorescent Indicators for Intracellular pH, Chem. Rev., 2010, 110, 2709-2728.*
International Search Report, PCT/KR2013/000089, May 31, 2013, pp. 1-7, obtained on Sep. 25, 2014.*
Fabiao, Yu et al., Chem.Commun., 2012, vol. 48, 2852-2854.

* cited by examiner

*Primary Examiner* — Christine T Mui
(74) *Attorney, Agent, or Firm* — Bachman & LaPointe, PC

(57) ABSTRACT

The present invention relates to a novel cyanne derivative having a meso-reaction functional group in a polymethine chain, and a preparation method thereof, and the cyanine derivative having the reaction functional group substituted at the meso site may be suitable for mass production thanks to a very simple synthesis method, have a very fast reaction rate because while a related art reagent for detection of nerve agents undergoes two steps of reactions, the cyanine derivative of the present invention undergoes only one step of reaction, have very excellent sensitivity, and be useful as an acid pH-activated ratiometric NIR probe because it is able to be activated in an acidic pH and is usable in an aqueous environment.

15 Claims, 10 Drawing Sheets

CYANINE DERIVATIVES HAVING MESO-REACTIVE FUNCTIONAL GROUP AT POLYMETHINE CHAIN AND PREPARATION METHOD THEREOF

TECHNICAL FIELD

The present disclosure relates to a novel cyanine derivative having a meso-reactive functional group at a polymethine chain, and a preparation method thereof.

BACKGROUND ART

Nerve agents are considered to be a heinous type in a chemical warfare. An organic phosphorous-based compound functioning as a class of important and fatal nerve agents is an important enzyme for a nerve system, and is a strong inhibitor of acetylcholinesterase (AChE) responsible for inhibition of acetylcholine, a neurotransmitter.

Phosphorylation of an active esteratic site of an enzyme residue by an organic phosphorous-based compound reagent causes an enzyme to be ineffective. Such an irreversible inactivation produces a large amount of acetylcholine as a result of cholinergic hyperstimulus, which leads to respiratory arrest and death within several minutes. Therefore, it is urgent to develop a method for sensitively and rapidly detecting nerve agents formed of a deadly poisonous, colorless and odorless organic phosphorous-based compound.

A design of a reactive chemosensor by esterification of an organic phosphorous-based compound nerve agent is a wise strategy in that it may rapidly detect a toxic organic phosphorous-based compound and such an approach may be used to decompose the organic phosphorous-based compound with high peculiarity.

A current method for detecting an organic phosphorous-based compound nerve agent is mainly based on colorimetric analysis, fluorescence analysis, electrochemical analysis, enzymatic analysis, or the like. However, such systems have limitations, such as low selectivity, slow reaction, complicated operation, and low portability.

Generally, since the colorimetric method uses an inexpensive apparatus, it is considered to be the simplest detection technique. The colorimetric method, however, always has a sensitivity issue at a low concentration.

In this regard, fluorescence modulation enables ideal high sensitivity signal detection. In particular, a ratiometric mode measuring the ratio of two wavelength strengths may enhance selectivity and sensitivity by removing perturbations from environmental effects.

Representative examples of organic phosphorous-based compound nerve agents are described below.

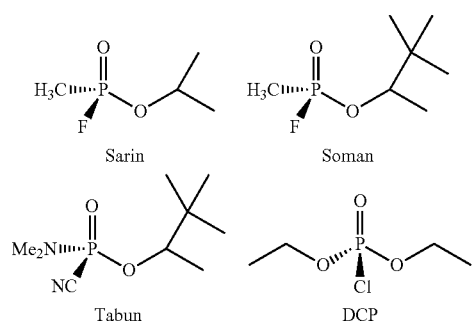

Sarin  Soman  Tabun  DCP

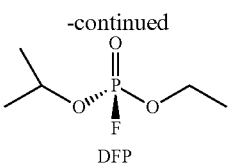

DFP

Meanwhile, a near-infrared ray (NIR) dye has come to prominence in analysis of many biological studies due to its optical properties able to image molecular activity with high penetration and low self-fluorescence background.

A tricarbocyanine dye is widely used as a fluorescent marker and a sensor for imaging in a living body because it has a high extinction coefficient and a comparatively high quantum yield, and the absorption and emission maxima occur in the near-IR region of the spectrum (650-900 nm).

Photophysical and structural properties of cyanine dyes depend on π-conjugated bridge between electron donor groups. Thus, a novel approach for cyanine dyes may be developed by disturbing a polymethine π-electron system of cyanine dyes. However, it is typically difficult to modify the cyanine structure through synthesis. Generally, a tricarbocyanine derivative is modified by nucleophillic substitution for substituting chlorine atom of tricarbocyanine having various functionalities at a meso site.

However, such a strategy is limited due to chlorine atom exhibiting a comparatively inactivity at the meso site. To avoid this limitation and to make better chemical and photochemical properties of tricarbocyanine as much as possible, a substituent having activity at the meso site of a polymethine chain is very preferable for designing various cyanine dyes.

Additionally, application of intercellular or extracellular pH change by various physiological and pathological processes is a promising strategy for analysis and diagnosis of cells. Since an infection or tumor generally makes an acidic environment, a small molecular fluorescent substance probe able to be activated in an acidic pH is a useful tool for detecting a cancer cell in an organism. However, up to now, there is almost no fluorescent probe able to be activated in an acidic pH for in vivo imaging.

Thus, the inventors of the present application have studied cyanine derivatives having a substituent having activity at a meso site of a polymethine chain, have found that the cyanine derivative having a reaction functional group substituted at the meso site is very simply synthesized, is suitable for mass production, has a very fast reaction rate because while a related art reagent for detection of nerve agents is subject to two steps of reactions, the cyanine derivative of the present invention is subject to only one step of reaction, has very excellent sensitivity, is able to be activated in an acidic pH, and is able to be used as an acid pH-activated ratiometric NIR probe, and have completed the present invention.

DISCLOSURE OF THE INVENTION

Technical Problem

One object of the present invention is to provide a novel cyanine derivative having a meso-reaction functional group at a polymethine chain.

Another object of the present invention is to provide a method of preparing the cyanine derivative.

Still another object of the present invention is to provide a chemosensor for detection of pH, including the cyanine derivative.

Even another object of the present invention is to provide a method of detecting pH change by using the cyanine derivative.

Yet another object of the present invention is to provide a chemosensor for detection of nerve agents, including the cyanine derivative.

Further another object of the present invention is to provide a method of detecting an organic phosphorous-based nerve agent by using the cyanine derivative.

Technical Solution

In order to achieve the objects, the present invention provides a novel cyanine derivative having a meso-reaction functional group at a polymethine chain expressed by the following formula 1:

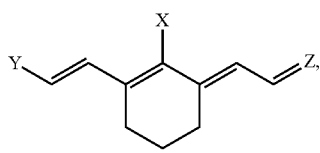

[Formula 1]

where X is —$NH_2$, —NCO, —NCS, —$N_3$,

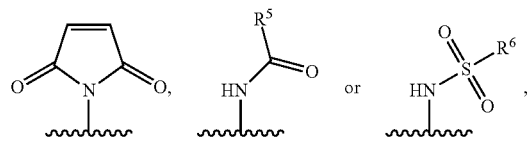

Y is

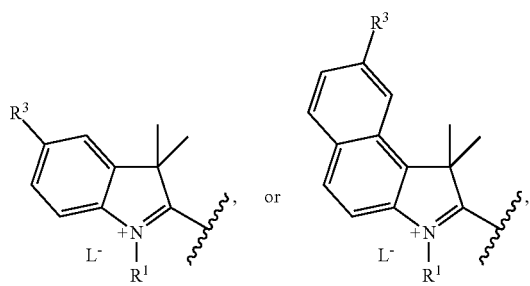

Z is

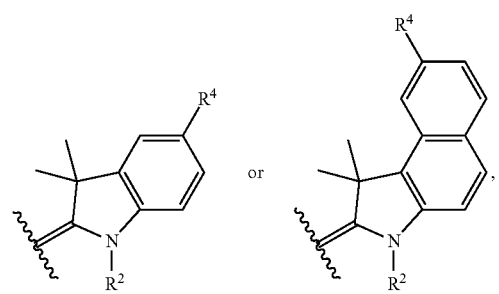

$L^-$ is $Cl^-$, $Br^-$, $I^-$, $ClO_4^-$ or $PF_6^-$, $R^1$ and $R^2$ are independently —$(CH_2)_n R^7$, —$(CH_2)_m OR^8$, —$(CHR^9 CH_2 O)_p R^8$ or

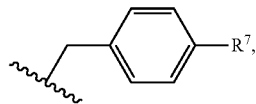

$R^3$, $R^4$ and $R^7$ are independently —H, —$SO_3 R^{10}$ or —$CO_2 R^{11}$, $R^5$ is

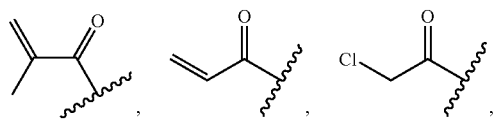

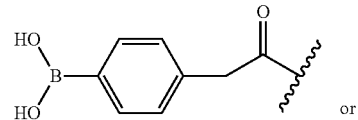

or

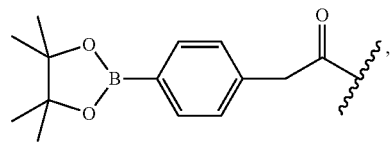

$R^6$ is

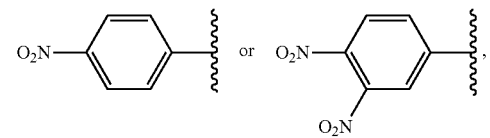

$R^8$ is —H or —$(CH_2)_q CH_3$, $R^9$ is —H or —$CH_3$, $R^{10}$ is —H or -M, $R^{11}$ is —H, -M or —$(CH_2)_q CH_3$,

M is Na, K or —$N(R^8)_4$, and m, n, p and q are independent integers ranging from 0 to 18.

Furthermore, the present invention provides a method of preparing a cyanine derivative, as described in the following reaction formula 1, the method including:

reacting compound 3 and phthalimide potassium in a first solvent to obtain compound 2 in which the phthalimide is substituted for a meso site of compound 3 (step 1); and reacting compound 2 prepared in step 1 and X—$NH_2$ in a second solvent to obtain compound 1 in which X is substituted for a meso site of compound 2 (step 2).

[Reaction formula 1]

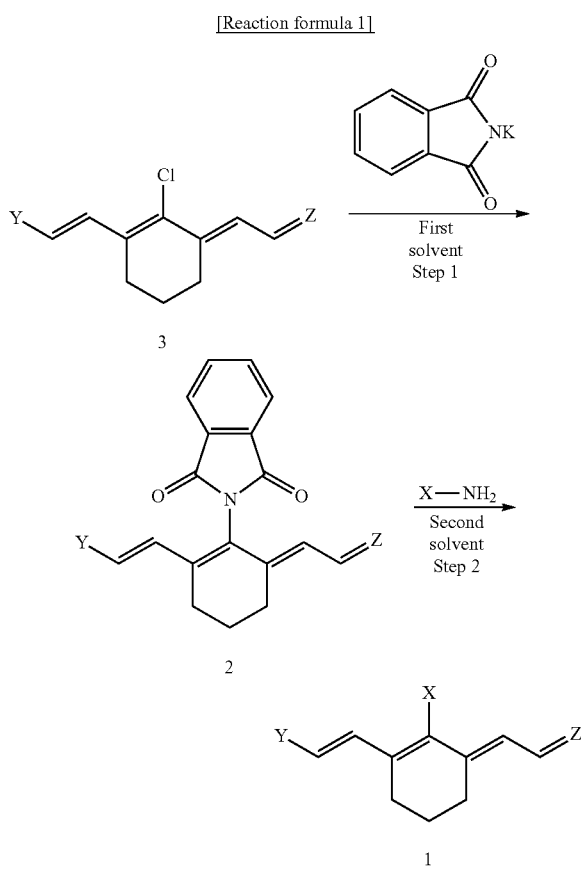

where X, Y and Z are those defined in formula 1.

Furthermore, the present invention provides a chemosensor for detection of pH, including a cyanine derivative expressed by formula 1, the chemosensor being characterized by being applied to paper, film or a particle-shaped substrate.

Furthermore, the present invention provides a method of detecting pH change characterized by measuring a change of decoloration, extinction or eradiation characteristic caused by a change of a π-conjugation system occurring when proton is added to a meso-reaction functional group of a polymethine chain of the cyanine derivative expressed by formula 1.

Furthermore, the present invention provides a chemosensor for detection of an organic phosphorous-based nerve agent, including a cyanine derivative expressed by formula 1, the chemosensor being characterized by being applied to paper, film or a particle-shaped substrate.

Furthermore, the present invention provides a method of detecting an organic phosphorous-based nerve agent characterized by measuring changes of decoloration, extinction and eradiation characteristics solely or in combination, caused by a change of a π-conjugation system occurring when a meso-reaction functional group of a polymethine chain of the cyanine derivative expressed by formula 1 undergoes a substitution reaction with an organic phosphorous-based nerve agent.

Advantageous Effects

The cyanine derivative according to the present invention may be suitable for mass production thanks to a very simple synthesis method, have a very fast reaction rate because while a related art reagent for detection of nerve agents undergoes two steps of reactions, the cyanine derivative of the present invention undergoes only one step of reaction, have very excellent sensitivity, and be useful as an acid pH-activated ratiometric NIR probe because it is able to be activated in an acidic pH and is usable in an aqueous environment.

MODE FOR CARRYING OUT THE INVENTION

Figure 1:
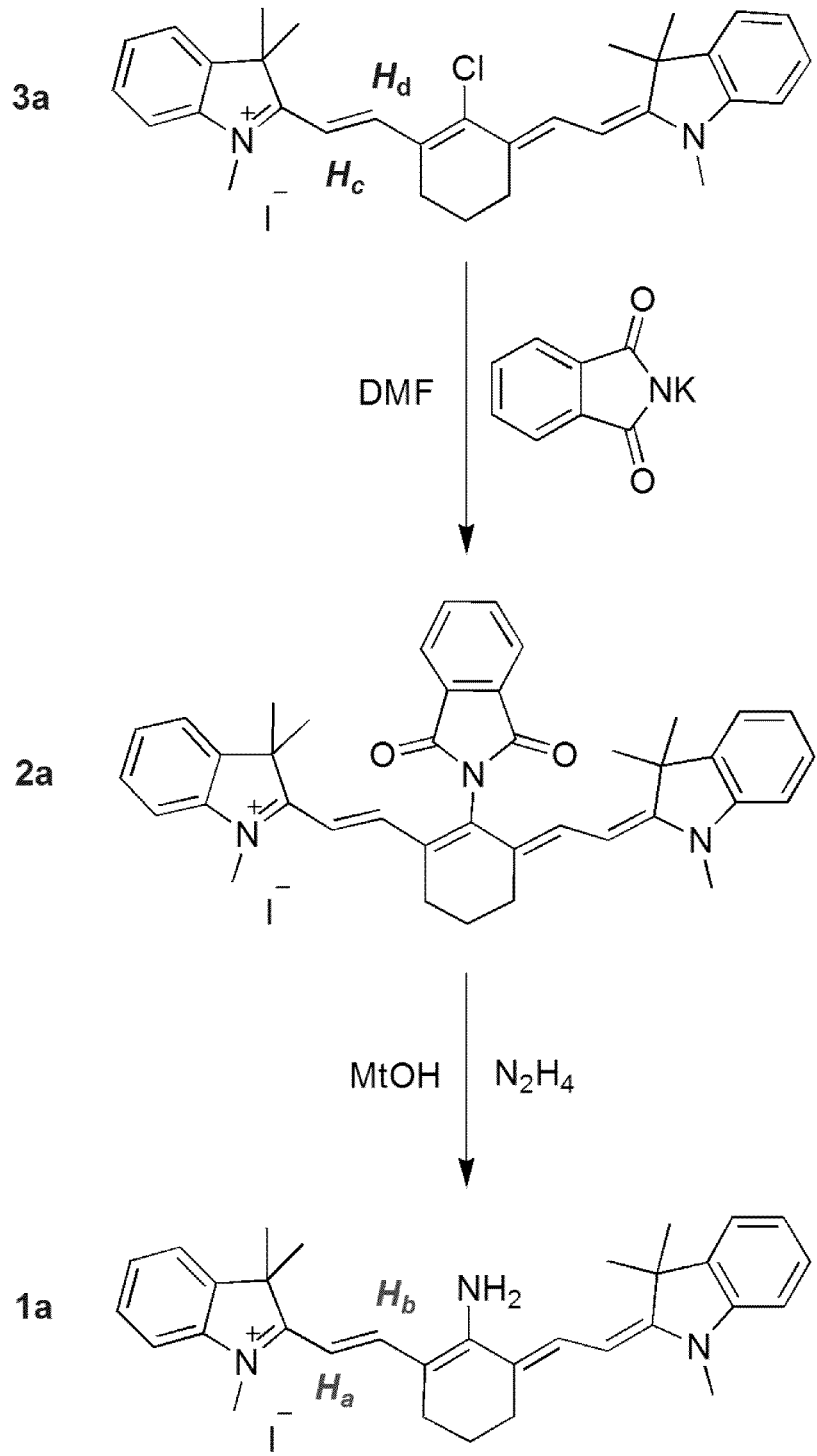
FIG. 1 is a reaction formula showing a preparation of compound 1a according to an embodiment of the present invention (substituted hydrogens in double bonds of compounds 1a and 3a are indicated by $H_a$, $H_b$, $H_c$, and $H_d$, respectively).

Hereinafter, the present invention will be described in detail.

The present invention provides a novel cyanine derivative having a meso-reaction functional group at a polymethine chain expressed by the following formula 1:

[Formula 1]

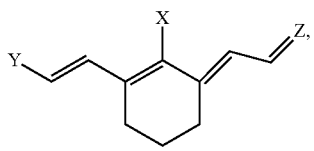

where X is —NH$_2$, —NCO, —NCS, —N$_3$,

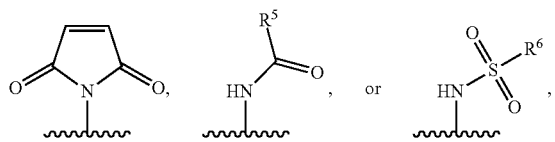

Y is

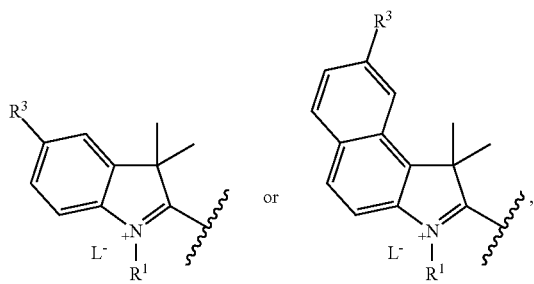

Z is

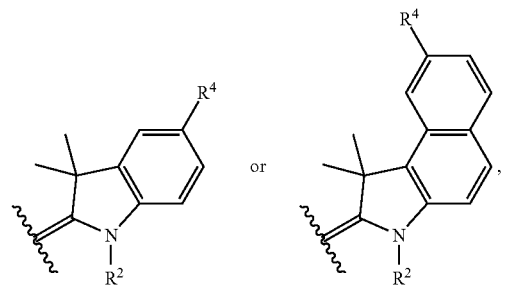

L$^-$ is Cl$^-$, Br$^-$, I$^-$, ClO$_4^-$ or PF$_6^-$,
R$^1$ and R$^2$ are independently —(CH$_2$)$_n$R$^7$, —(CH$_2$)$_m$OR$^8$, —(CHR$^9$CH$_2$O)$_p$R$^8$ or

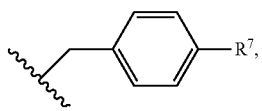

R$^3$, R$^4$ and R$^7$ are independently —H, —SO$_3$R$^{10}$ or —CO$_2$R$^{11}$,
R$^5$ is

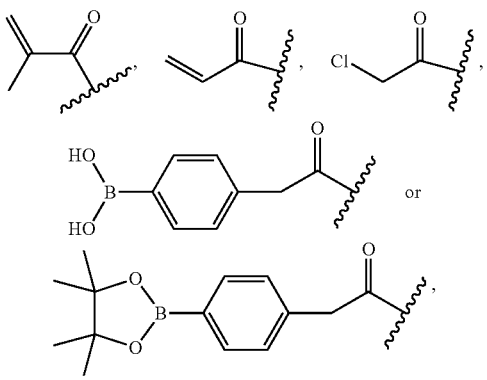

R$^6$ is

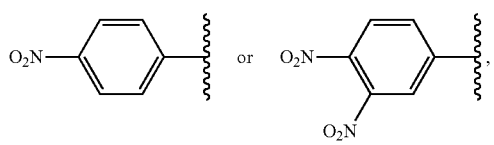

R$^8$ is —H or —(CH$_2$)$_q$CH$_3$,
R$^9$ is —H or —CH$_3$,
R$^{10}$ is —H or -M,
R$^{11}$ is —H, -M or —(CH$_2$)$_q$CH$_3$,
M is Na, K or —N(R$^8$)$_4$, and
m, n, p and q are independent integers ranging from 0 to 18.

Preferably, X is —NH$_2$, —NCO, —NCS, or —N$_3$,
Y is

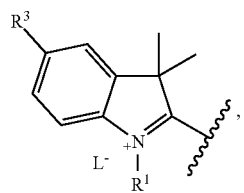

Z is

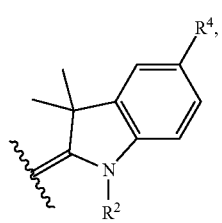

L$^-$ is Cl$^-$, Br$^-$ or I$^-$,
R$^1$ and R$^2$ are independently —(CH$_2$)$_n$R$^7$, —(CH$_2$)$_n$OR$^8$, or —(CHR$^9$CH$_2$O)$_p$R$^8$,
R$^3$, R$^4$ and R$^7$ are independently —H, or —CO$_2$R$^{11}$, $R^5$ is

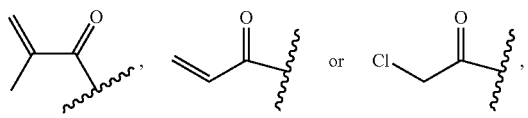

$R^6$ is

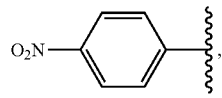

$R^8$ is —H or —$(CH_2)_q CH_3$,
$R^9$ is —H or —$CH_3$,
$R^{10}$ is —H or -M,
$R^{11}$ is —H or -M,
M is Na or K, and
m, n, p and q are independent integers ranging from 0 to 10.
More preferably,
X is —$NH_2$, or —NCO,
Y is

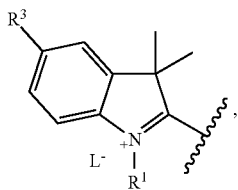

Z is

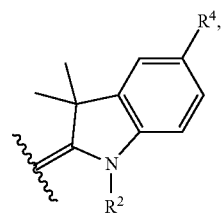

$L^-$ is $Cl^-$, $Br^-$ or $I^-$,
$R^1$ and $R^2$ are independently $C_{1-3}$ straight chain alkyl,
$R^3$ and $R^4$ are independently —H or —$CO_2H$.
Most preferably,
X is —$NH_2$,
Y is

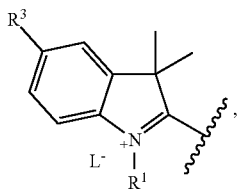

Z is

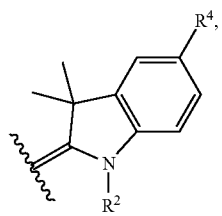

$L^-$ is $I^-$,
$R^1$ and $R^2$ are —$CH_3$, and
$R^3$ and $R^4$ are —H.

A novel cyanine derivative having a meso-reaction functional group at a polymethine chain according to the present invention induces a change of decoloration, absorbance and luminescence characteristics while when the cyanine derivative reacts with other compounds, a π-conjugation system formed at the polymethine chain is varied, because the meso-reaction functional group (which indicates X in the definition of substituents of formula 1) has a high activity and easily reacts with other compounds.

A substance intended to detect may be analyzed qualitatively/quantitatively by using an analysis method, such as a colormetric analysis, an absorption analysis, a luminescence analysis or the like using the change characteristics.

The cyanine derivative according to the present invention may be suitable for mass production thanks to a very simple synthesis method, have a very fast reaction rate because while a related art reagent for detection of nerve agents undergoes two steps of reactions, the cyanine derivative of the present invention undergoes only one step of reaction (nucleophillic substitution reaction of the meso-reaction functional grope and a substance intended to detect, have very excellent sensitivity, and be useful as an acid pH-activated ratiometric NIR probe because it is able to be activated in an acidic pH and is usable in an aqueous environment.

Also, the present invention provides a method of preparing the cyanine derivative expressed by the following reaction formula 1, the method including:

reacting compound 3 and phthalimide potassium in a first solvent to obtain compound 2 in which the phthalimide is substituted at a meso site of compound 3 (step 1); and reacting compound 2 prepared in step 1 and X—$NH_2$ in a second solvent to obtain compound 1 in which X is substituted at a meso site of compound 2.

[Reaction formula 1]

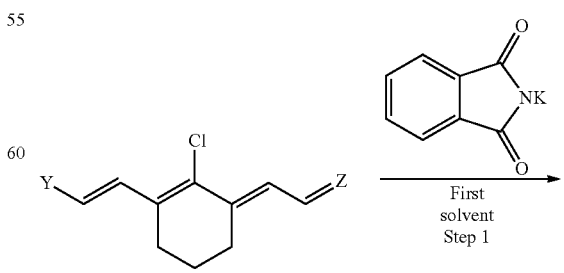

3

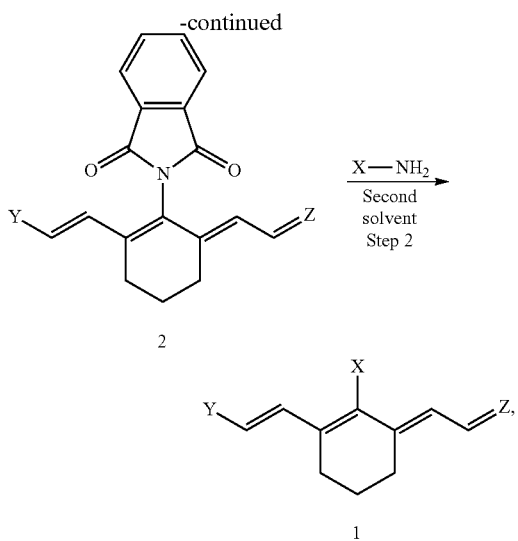

where X, Y and Z are those defined in formula 1.

The cyanine derivative according to the present invention may be simply prepared by using a Gabriel synthesis.

In the preparation method according to the present invention, the first solvent may include, but be not limited to, dimethylformamide, dimethylacetamide, dimethylether, tetrahydrofuran, 1,4-dioxane, benzene, toluene, and the like.

In the preparation method according to the present invention, the second solvent may include, but be limited to, lower alcohols, such as methanol, ethanol, propanol, butanol, and the like.

Further, the present invention provides a chemosensor for detection of pH, including a cyanine derivative expressed by formula 1.

At this time, the chemosensor may be applied to, but limited to, paper, film or a particle-shaped substrate.

Also, the present invention provides a method of detecting pH change using a cyanine derivative expressed by the above-mentioned formula 1.

At this time, the method of detecting pH change is characterized by measuring a change of decoloration, absorbance or luminescence characteristic caused by a change of a π-conjugation system occurring when proton is added to a meso-reaction functional group of a polymethine chain of the cyanine derivative expressed by formula 1.

Further, the present invention provides a chemosensor for detection of an organic phosphorous-based nerve agent, including a cyanine derivative expressed by formula 1.

At this time, the chemosensor may be applied to, but limited to, paper, film or a particle-shaped substrate.

Herein, examples of the detectable organic phosphorous-based nerve agents may include sarin, soman, tabun, diethylchlorophosphate (DCP), diisopropylfluorophosphate (DFP), and the like.

Also, the present invention provides a method of detecting an organic phosphorous-based nerve agent using a cyanine derivative expressed by the above-mentioned formula 1.

At this time, the method of detecting an organic phosphorous-based nerve agent is characterized by measuring changes of decoloration, extinction and eradiation characteristics solely or in combination, caused by a change of a π-conjugation system occurring when a meso-reaction functional group of a polymethine chain of the cyanine derivative expressed by formula 1 undergoes a substitution reaction with an organic phosphorous-based nerve agent.

Hereinafter, the present invention will be described in more detail through the following examples. The following examples should not be construed as limiting the present invention, rather they are provided for exemplarily describing the present invention.

Preparation Example 1

Preparation of Cyanine-C1 (3)

Preparation of (E)-2-chloro-3-(hydroxymethylene)cyclohex-1-enecarbaldehyde

Anhydride dimethylformamide (20 ml) was added to $CH_2Cl_2$ (20 ml) in an N2 atmosphere, and they are stirred at 0° C., and then a mixture solution of $CH_2Cl_2$ (10 ml) and $POCl_3$ (20 ml) was added dropwise in an ice bath. After 30 minutes, cyclohexane (5 g, 50 mmol) was added to obtain a reaction mixture, and the reaction mixture was refluxed while strongly stirring for 3 hours at 80° C. Thereafter, the mixture solution was poured in an ice water, and was left overnight to obtain a yellow solid (6.2 g, 70%) of (E)-2-chloro-3-(hydroxymethylene)cyclohex-1-enecarbaldehyde.

$^1$H-NMR (300 MHz, $CDCl_3$): δ=1.65 (m, 2H), 2.31 (t, 4H, J=6.3 Hz), 10.21 (s, 1H).

Preparation of Cyanine-C1

1,2,3,3-tetramethyl-3H-indolinium iodide (6.3 g, 0.021 mol) and (E)-2-chloro-3-(hydroxymethylene)cyclohex-1-enecarbaldehyde prepared previously were dissolved in a butanol-benzene (70 ml-20 ml) solvent in an $N_2$ atmosphere. The mixture solution was refluxed for 8 hours at 140° C. Thereafter, a solvent was evaporated to obtain a solid mixture, and the obtained solid mixture was recrystallized using methanol to obtain compound 3 (cyanine-C1) in a green solid form (4.5 g, 74%).

$^1$H NMR (300 MHz, $CD_3Cl_3$, ppm) δ=1.73 (s, 12H, $CH_3$), 1.97 (m, 2H, cyclohexane-H), 2.75 (m, 4H, cyclohexane-H), 3.75 (s, 6H, $NCH_3$), 6.23 (d, J=14.2 Hz, 2H, alkene-H), 7.20 (d, d=7.8 Hz, 2H, Ph-H), 7.25 (t, d=7.8 Hz, 2H, Ph-H), 7.37-7.41 (m, 4H, Ph-H), 8.35 (d, J=14.1 Hz, 2H, alkene-H).

Example 1

Preparation of Cyanine-Amine (1a)

Preparation of Cyanine-Phthalimide (2)

Compound 3 (500 mg, 0.75 mmol) prepared in Preparation Example 1, and phthalimide potassium (166 mg, 0.90 mmol) were dissolved in anhydride dimethylformamide (15 ml), and the mixture was heated in an $N_2$ atmosphere at about 80-90° C. for 5 hours. A red solid obtained by evaporating the solvent was purified by a flash silica chromatography to obtain compound 2 (cyanine-phthalimide) in a red solid form (280 mg, 49%).

$^1$H NMR (300 MHz, $CD_3Cl_3$) (ppm): δ=1.63 (s, 12H, —$CH_3$), 1.91 (m, 2H, cyclohexane-H), 2.64 (t, J=5.4 Hz, 4H, cyclohexane-H), 3.23 (s, 6H, $NCH_3$), 5.43 (d, J=13.2 Hz, 2H, alkene-H), 6.71 (d, J=7.8 Hz, 2H, Ph-H), 6.93 (t, J=7.5 Hz, 2H, Ph-H), 7.20 (t, J=7.5 Hz, 4H, Ph-H), 7.76-7.80 (m, 2H, Ph-H), 7.88-7.91 (m, 2H, Ph-H), 8.19 (d, J=13.2 Hz, 2H, alkene-H).

Preparation of Cyanine-Amine (1a)

Compound 2 (cyanine-phthalimide) (280 mg) prepared previously and hydrazine hydrate (1 ml) were dissolved in methanol (15 ml), and the mixture was heated in an N2 atmosphere at about 60-70° C. for 3 hours. After the solvent was evaporated, CH2Cl2 was added to obtain a large amount of white solid precipitate. A red solid obtained by filtering and evaporating the mixture solution was purified by a flash silica chromatography to obtain compound 1a (cyanine-amine) in a red solid form (150 mg, 63%).

$^1$H NMR (300 MHz, CD$_3$Cl$_3$) (ppm): δ=1.69 (s, 12H, —CH$_3$), 1.89 (m, 2H, cyclohexane-H), 2.63 (t, J=5.4 Hz, 4H, cyclohexane-H), 3.23 (s, 6H, NC$\underline{H_3}$), 5.43 (d, J=13.2 Hz, 2H, alkene-H), 6.71 (d, J=7.8 Hz, 2H, Ph-H), 6.95 (t, J=6.9 Hz, 2H, Ph-H), 7.18-7.24 (m, 4H, Ph-H), 8.19 (d, J=13.2 Hz, 2H, alkene-H).

$^{13}$C-NMR (75 MHz, CD$_3$Cl$_3$, ppm): δ=14.2064, 21.0653, 22.5523, 25.8685, 28.7071, 29.2873, 46.4402, 60.4072, 92.5391, 106.4178, 120.4795, 121.7382, 126.8638, 127.6369, 132.7425, 139.6232, 144.6192, 163.2035, 186.4762 (19 C).

Fabs Mass (positive): [C$_{32}$H$_{38}$IN$_3$—I]$^+$ Calculated: 464.3066. Found: 463.3062.

Experimental Example 1

Evaluation of Change of π-Conjugation System

To check a change of a π-conjugation system occurring when a chlorine group in the meso site of compound 3a was substituted by an amine group in the course of preparing compound 1a of Example 1, an experiment was performed as follows.

Specifically, to check a change of a π-conjugation system in relation to the repulsion and attraction of compounds 1a and 3a, a chemical shift of specific hydrogens (indicated by H$_a$ and H$_b$ in compound 1a, and by H$_c$ and H$_d$ in compound 3a) substituted in a double bond was measured using $^1$H NMR (Manufacturer: Brucker, Model: AM-300). A simple process of preparing compound 1a from a starting material of compound 1a through a Gabriel reaction is shown in FIG. 1, in which hydrogens substituted in the double bonds for which chemical movements in compounds 1a and 3a were measured were indicated by H$_a$, H$_b$, H$_c$, and H$_d$, respectively.

FIG. 1 is a reaction formula showing a preparation of compound 1a according to an embodiment of the present invention (substituted hydrogens in double bonds of compounds 1a and 3a are indicated by H$_a$, H$_b$, H$_c$, and H$_d$, respectively).

As shown in FIG. 1, an apparent chemical movement of hydrogens substituted in double bonds of compounds 1a and 3a can be confirmed from a $^1$H-NMR spectrum analysis of a cyanine derivative (Compound 1a: δ$_{Ha}$=5.43 ppm and δ$_{Hb}$=8.19 ppm; Compound 3a: δ$_{Hc}$=6.23 ppm and δ$_{Hd}$=8.35 ppm). These results show that the π-conjugation system undergoing repulsion and attraction during the synthesis of compound 1a from compound 3a has been drastically varied with rearrangement of electron distribution.

Experimental Example 2

Evaluation of Hypsochromic Shift

Generally, electron donating or withdrawing property of a meso-substituent has an influence on absorbance spectra of a polymethine dye, but does not have a great influence on luminescence spectra. To check changes of absorbance and luminescence spectra according to a hypsochromic shift occurring when a chlorine group in the meso site of compound 3a was substituted by an amine group in the course of preparing compound 1a of Example 1, an experiment was performed as follows.

Specifically, absorbance spectra of 5 μM compounds 3a and 1a were measured in methanol of 25° C. by using a UZV/VIS spectrometer (Manufacturer: Scinco, Model: 3000 spectrophotometer). Also, luminescence spectra of compounds 3a and 1a were measured in the same condition by using a fluorescent spectrometer (Manufacturer: Shimada, Model: RF-5301/PC). The measurement results of the absorbance and luminescence spectra are shown in FIG. 2.

Figure 2:
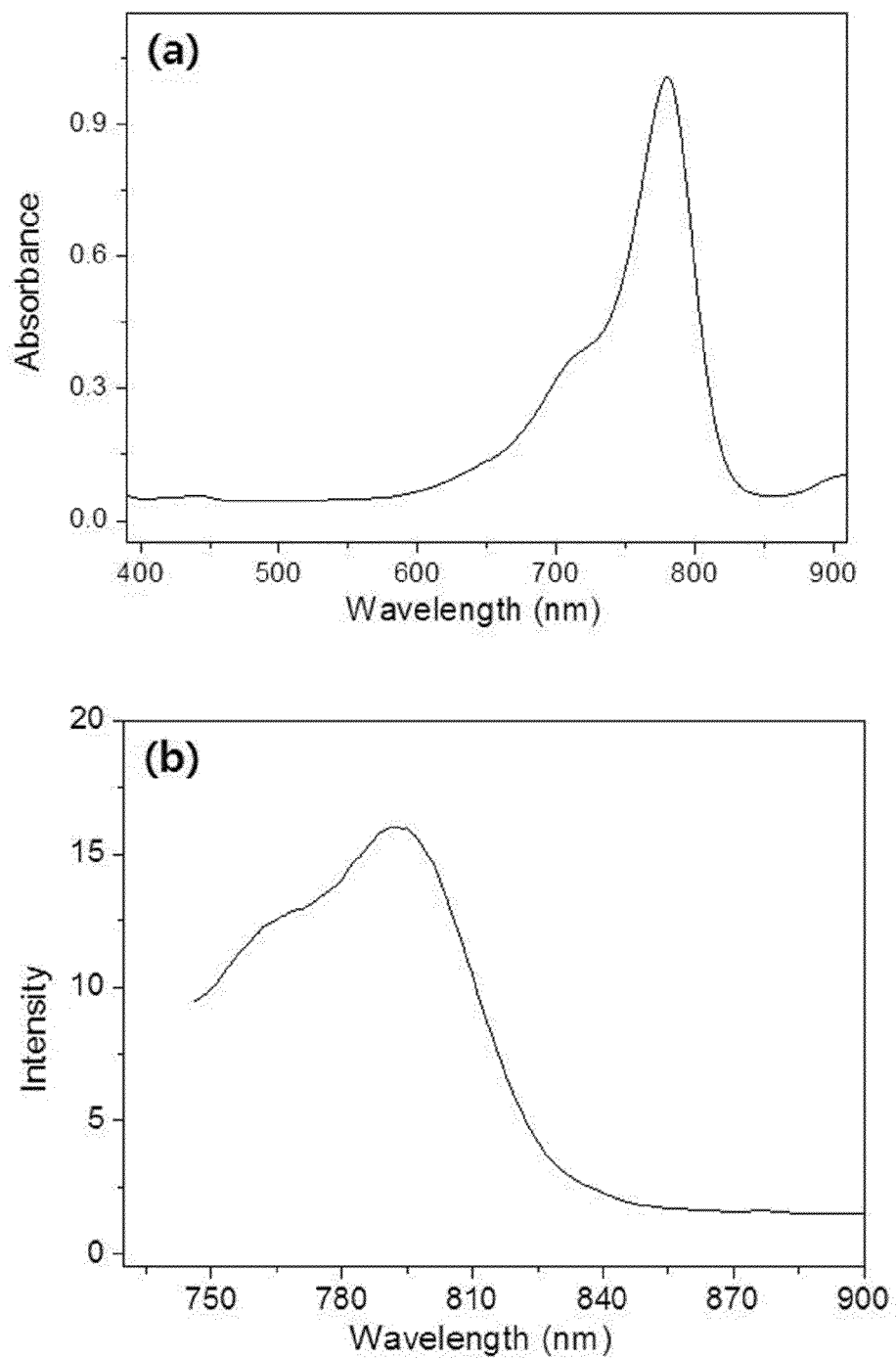
FIG. 2 are graphs showing the absorbance and luminescence spectra of compound 3a prepared in preparation example 1 ((a) is the absorbance spectra, and (b) is the luminescence spectra).

FIG. 2 are graphs showing the absorbance and luminescence spectra of compound 3a prepared in preparation example 1 ((a) is the absorbance spectra, and (b) is the luminescence spectra).

Figure 3:
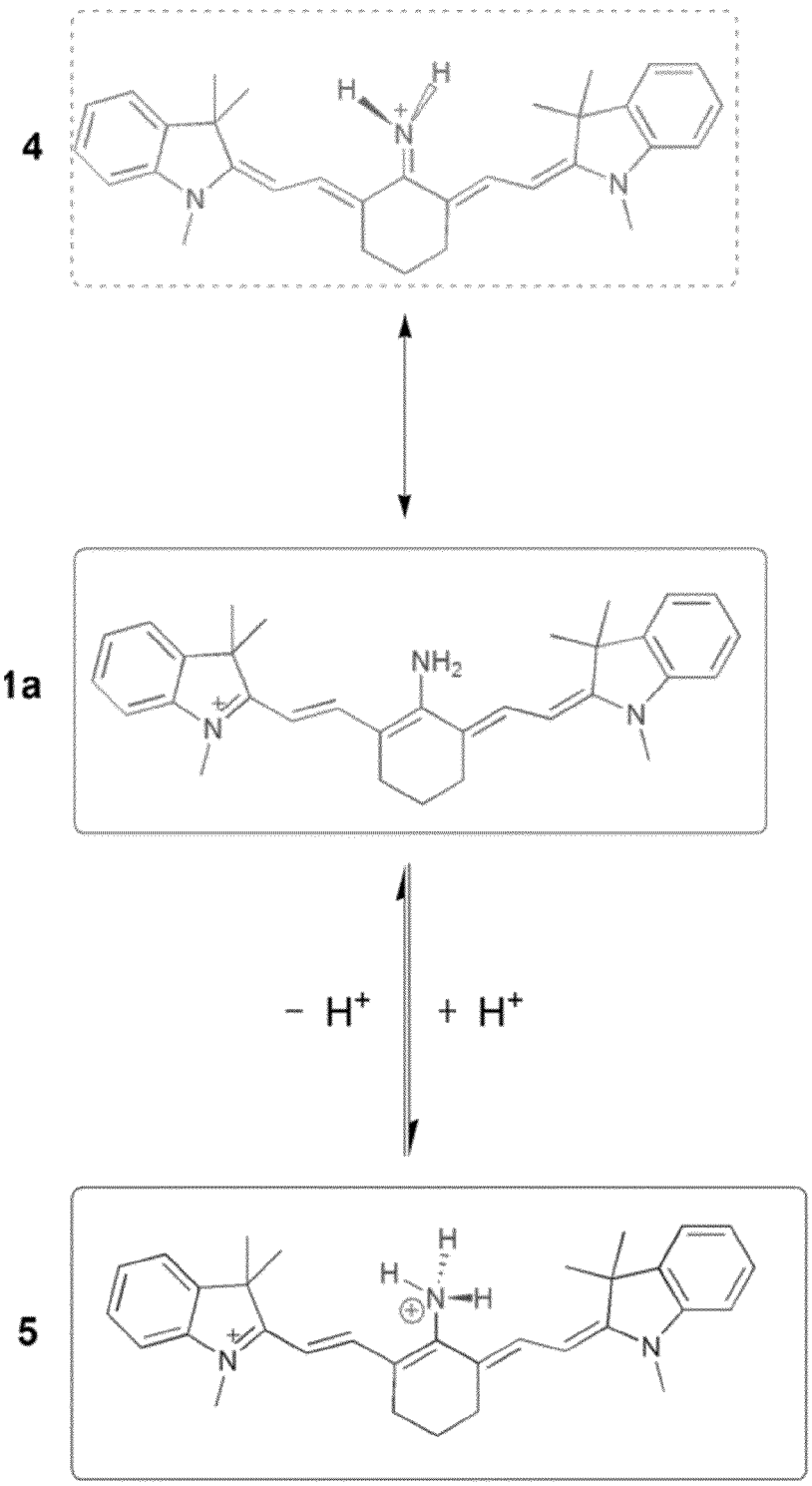
FIG. 3 is a an image showing that a π-conjugation system formed at a polymethine chain of compound 1a is varied by a meso-reaction functional group (Compounds 4 and 1a show a change of the π-conjugation system by tautomerization, and compounds 5 and 1a a change of the π-conjugation system according to pH change).

FIG. 3 is a an image showing that a π-conjugation system formed at a polymethine chain of compound 1a is varied by a meso-reaction functional group (Compounds 4 and 1a show a change of the π-conjugation system by tautomerization, and compounds 5 and 1a a change of the π-conjugation system according to pH change).

As shown in FIG. 2, it was confirmed that compound 1a (λ$_{abs}$=570 nm) prepared in Example 1 in the absorbance spectra exhibited a strong hypsochromic shift of about 210 nm, compared with compound 3a (λ$_{abs}$=780 nm) prepared in Preparation Example 1. Also, it was confirmed that compound 1a (λ$_{ex}$=630 nm) prepared in Example 1 in the luminescence spectra exhibited a strong hypsochromic shift of about 160 nm, compared with compound 3a (λ$_{ex}$=790 nm) prepared in Preparation Example 1.

As shown in FIG. 3, the π-conjugation system of compound 3a has a positive charge while an electron is shifted to other site between two nitrogen atoms, whereas in the π-conjugation system of compound 1a, tautomerization occurs in which an amine group existing at the meso site and having abundance of electrons donates electrons to adjacent nitrogen atoms having a positive charge through the π-conjugation system. Also, it can be known that compound 1a according to the present invention causes a change in the π-conjugation system according to pH change.

Therefore, since a large hypsochromic shift occurs even in the luminescence spectra, the cyanine derivative according to the present invention has an advantage in that it may be applied to a high sensitive fluorescent analysis.

Experimental Example 3

Evaluation of Change of Absorbance/Luminescence Spectra According to pH Change

To check that the absorbance/luminescence spectra of compound 1a prepared in Example 1 is varied according to pH change, an experiment was performed as follows.

Absorbance/luminescence spectra of compound 1a (5 μM) prepared in Example 1 were measured in a mixture solution of CH$_3$OH—H$_2$O (volume ratio: 1-1) having various pH values (e.g., 9.69, 6.96, 4.13, 3.56, 3.24, 2.98, 2.77 and 1.87) by using the equipments used in Experimental Example 2.

Figure 4:
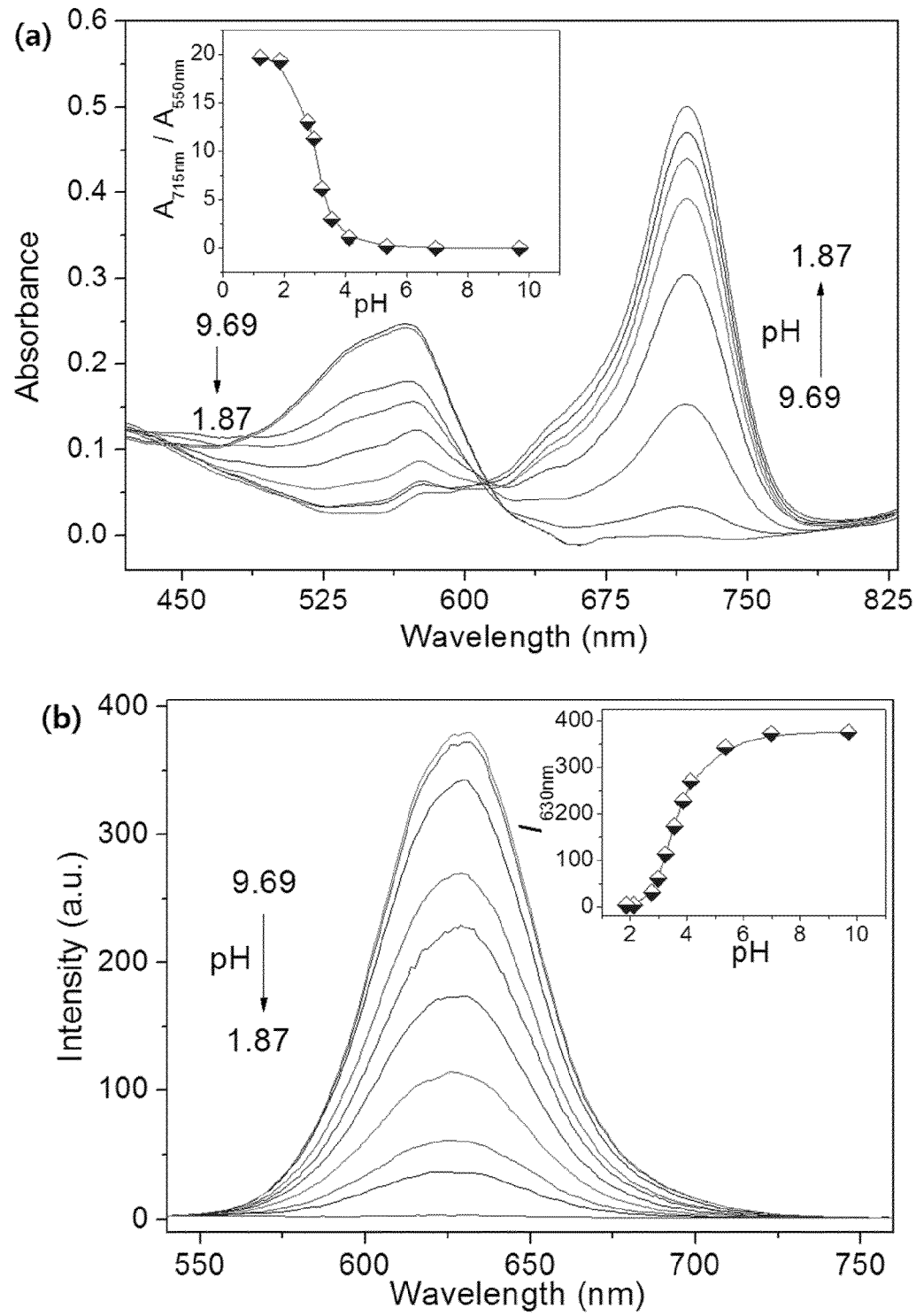
FIG. 4 are graphs showing the absorbance and luminescence spectra of compound 1a according to an embodiment of the present invention (FIG. 4 (a) is the absorbance spectra, the inserted picture in FIG. 4 (a) is a graph showing a ratio ($A_{715\ nm}/A_{550\ nm}$) of absorbance intensities, FIG. 4 (b) is the luminescence spectra, and the inserted picture in FIG. 4 (b) is a graph showing a change of fluorescent intensity at 630 nm).

FIG. 4 are graphs showing the absorbance and luminescence spectra of compound 1a according to an embodiment of the present invention (FIG. 4 (*a*) is the absorbance spectra, the inserted picture in FIG. 4 (*a*) is a graph showing a ratio (A$_{715\ nm}$/A$_{550nm}$) of absorbance intensities, FIG. 4 (*b*) is the luminescence spectra, and the inserted picture in FIG. 4 (*b*) is a graph showing a change of fluorescent intensity at 630 nm).

Figure 5:
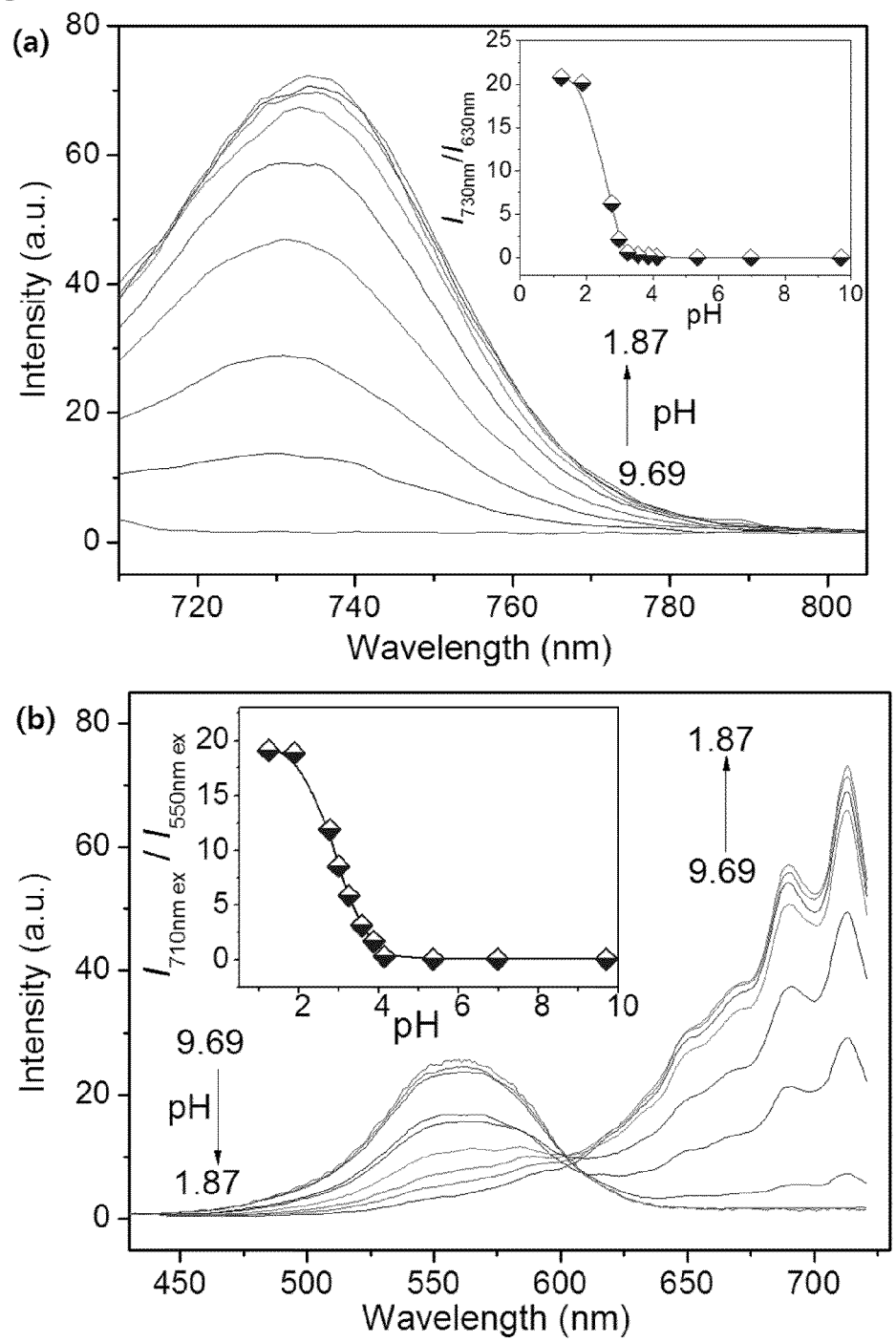
FIG. 5 is graphs showing luminescence spectra of compound 1a according to an embodiment of the present invention (FIG. 5 (a) is the luminescence spectra ($\lambda_{ex}$=710 nm), the inserted picture in FIG. 5 (a) is a graph showing a ratio ($I_{730\ nm}/I_{630\ nm}$) of fluorescent intensities as a function of pH in a luminescence spectra mode, FIG. 5 (b) is the luminescence spectra ($\lambda_{ex}$=730 nm), and the inserted picture in FIG. 5 (b) is a graph showing a ratio ($I_{710\ nm\ ex}/I_{550\ nm\ ex}$) of fluorescent intensities as a function of pH together with $\lambda_{em}$=730 nm in an excitation spectra mode).

FIG. 5 is graphs showing luminescence spectra of compound 1a according to an embodiment of the present invention (FIG. 5 (a) is the luminescence spectra ($\lambda_{ex}$=710 nm), the inserted picture in FIG. 5 (a) is a graph showing a ratio ($I_{730\ nm}/I_{630\ nm}$) of fluorescent intensities as a function of pH in a luminescence spectra mode, FIG. 5 (b) is the luminescence spectra ($\lambda_{ex}$=730 nm), and the inserted picture in FIG. 5 (b) is a graph showing a ratio ($I_{(710\ nm\ ex)}/I_{(550\ nm\ ex)}$) of fluorescent intensities as a function of pH together with $\lambda_{em}$=730 nm in an excitation spectra mode).

As shown in FIGS. 4 and 5, a lone electron pair in a nitrogen atom of the amine group existing in compound 1a is easily influenced by addition of proton and exhibits pH dependence. As shown in FIGS. 4 (a) and (b), compound 1a has absorbance (570 nm) and luminescence (630 nm) in the mixture solution of $CH_3OH$—$H_2O$ (volume ratio: 1-1). At a low pH value, the absorbance peak at 570 nm ($\epsilon$=5×10$^4$ $M^{-1}\cdot cm^{-1}$)) was drastically decreased due to addition of proton, and a new strong band was observed at 715 nm ($\epsilon$=1×10$^5$ $M^{-1}\cdot cm^{--1}$) in the reference of an isosbestic point at 610 nm (FIG. 4 (a)). Likewise, as the pH value is reduced in the luminescence spectra of FIG. 4 (b), the peak at 630 nm was drastically decreased, and in the luminescence spectra of FIG. 5 (a), a new near-infrared ray band appeared at 630 nm.

Also, an acid dissociation constant ($pK_a$) value was presumed by adjusting pH change and a change of luminescence intensities ($I_{630\ nm}$ or $I_{730\ nm}$ in the inserted picture of FIG. 5 (a)) according to the absorbance ratio ($A_{715\ nm}/A_{550\ nm}$ in the inserted image of FIG. 4 (a)). A ratiometric fluorescence function may be established using two channels (luminescence and excitation spectra modes). The ratiometric function of the excitation spectra is a function of pH change value, and was obtained from the fluorescence ratio ($I_{710\ nm\ ex}/I_{550\ nm\ ex}$) observed at 730 nm (FIG. 5 (b)). The results exhibited that an acid dissociation constant ($pK_a$) of compound 1a was about 3.6.

Therefore, compound 1a prepared in Example 1 may be used as an acid pH-activatable ratiometric NIR probe that may be used as a useful tool for in vivo imaging based on measurement of two ratios of changes of absorbance and luminescence.

Experimental Example 4

Colorimetric Evaluation According to Organic Phosphorous-Based Nerve Agent

An organic phosphorous-based nerve agent used as a fatal poison gas in chemical warfare has a chemical structure having a leaving group positioned at a center of 4-substituted phosphorous. To check whether compound 1a prepared in Example 1 is decolored when reacted with an organic phosphorous-based nerve agent, an experiment was performed as follows.

Specifically, diethylchlorophosphate (DCP) which has a similar structure to an existing nerve gas but excludes toxicity was used in the experiment. Compound 1a prepared in Example 1, and DCP were put in a CH2Cl2 solvent and were reacted at room temperature to observe a change of color, and results are shown in FIG. 6.

Figure 6:
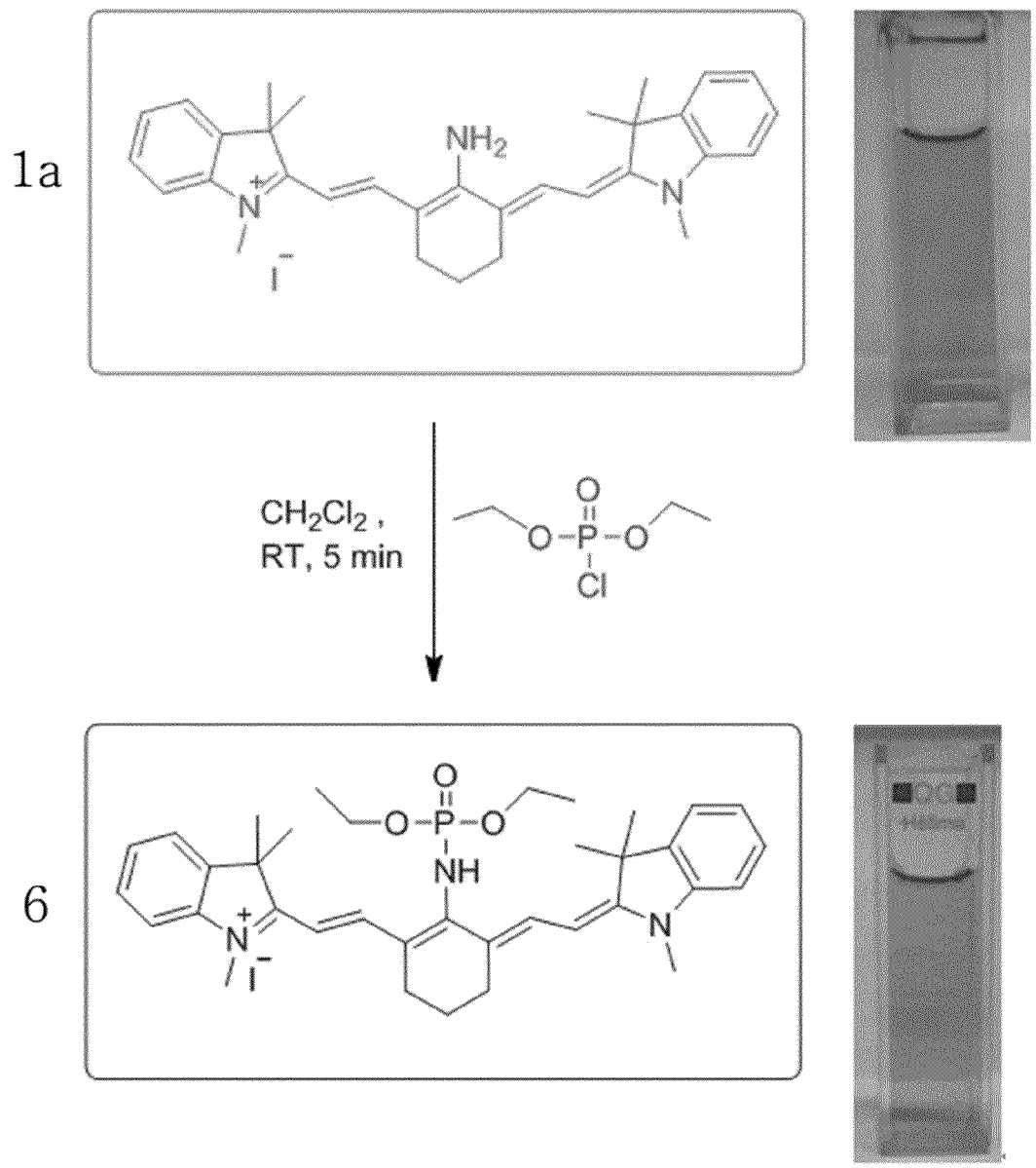
FIG. 6 shows a structure and a color change of a compound generated by a reaction of compound 1a according to an embodiment of the present invention with a nerve poison gas analog DCP.

FIG. 6 shows a structure and a color change of a compound generated by a reaction of compound 1a according to an embodiment of the present invention with a nerve poison gas analog DCP.

As shown in FIG. 6, when only compound 1a existed in the $CH_2Cl_2$ solvent, the generated compound was purple, but when DCP was added to the $CH_2Cl_2$ solvent, it was confirmed that as DCP was substituted at the meso site, the generated compound was changed to bright sky-blue.

Therefore, the cyanine derivative according to the present invention can be easily detected because it is decolored when reacted with an organic phosphorous-based nerve poison gas, and even the concentration of the cyanine derivative can be measured.

Experimental Example 3

Evaluation of Change of Absorbance/Luminescence Spectra According to Organic Phosphorous-Based Nerve Agent To check whether the fluorescence spectrum of compound 1a prepared in Example 1 is changed when compound 1a reacted with an organic phosphorous-based nerve agent, an experiment was performed as follows.

Specifically, 2 ppm of diethylchlorophosphate (DCP) (1 ppm—5.8×10$^{-6}$ M) was added to a $CH_2Cl_2$ mixture solution containing compound 1a (2 μM)) prepared in Example 1, and then absorbance and luminescence spectra of the generated compound were measured using the absorbance/luminescence spectrometer used in Experimental Example 2. Measurement results are shown in FIG. 7.

Figure 7:
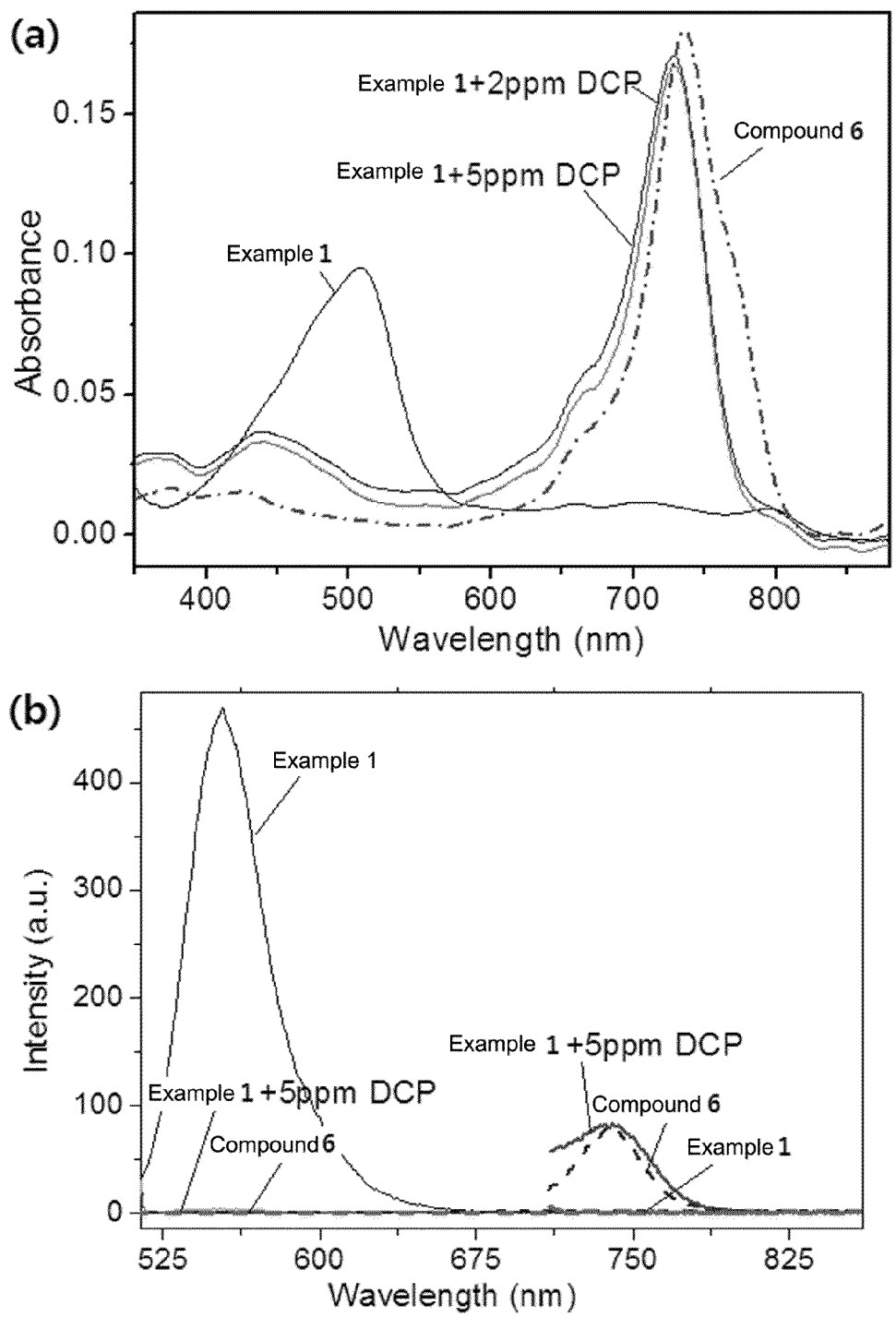
FIG. 7 are graphs showing absorbance spectra (a) and luminescence spectra (b) occurring when compound 1a according to an embodiment of the present invention reacts with a nerve poison gas analog DCP.

FIG. 7 are graphs showing absorbance spectra (a) and luminescence spectra (b) occurring when compound 1a according to an embodiment of the present invention reacts with a nerve poison gas analog DCP.

As shown in FIG. 7, it was confirmed that after DCP (2 ppm) was added, a new acuate band was rapidly generated at 730 nm within a few seconds and an initial band at 510 nm disappeared (FIG. 7 (a)). Also, it was confirmed that as the luminescence peak at a short wavelength of 550 nm was sharply reduced, a new near-infrared ray luminescence was rapidly generated at 740 nm. These results proved that DCP underwent a rapid substitution reaction at the meso site of compound 1a to form phosphate ester.

Thus, since the cyanine derivative according to the present invention rapidly reacts with an organic phosphorous-based nerve agent within a few seconds to change the absorbance and luminescence spectra, it can easily detect the organic phosphorous-based nerve agent in spectroscopy.

Experiment Example 6

Evaluation of Reactivity with Organic Phosphorous-Based Nerve Agent in Aqueous Condition In aqueous condition, development of a chemosensor for an organic phosphorous-based nerve agent remains as a challenging task. So, to check whether or not compound 1a prepared in Example 1 reacts with DCP in aqueous condition, an experiment was performed as follows.

Specifically, to avoid pH fluctuation due to a partial hydrolysis of DCP and minimize pH change by hydrochloric acid that is a byproduct generated by reaction of compound 1a and DCP, HEPES buffer (pH=7.4) was used in the experiment. Compound 1a (2 μM), HCl (2×10$^{-3}$ M) and DCP (50 ppm, 3×10$^{-4}$ M) were added respectively or at the same time in a mixture solution of $CH_3OH/H_2O$ (volume ratio: 80/20) and HEPES buffer (10 mM, pH=7.4), and absorbance/luminescence spectra of the generated compounds were measured using the absorbance/luminescence spectrometer used in Experimental Example 2. Measurement results are shown in FIG. 8.

Figure 8:
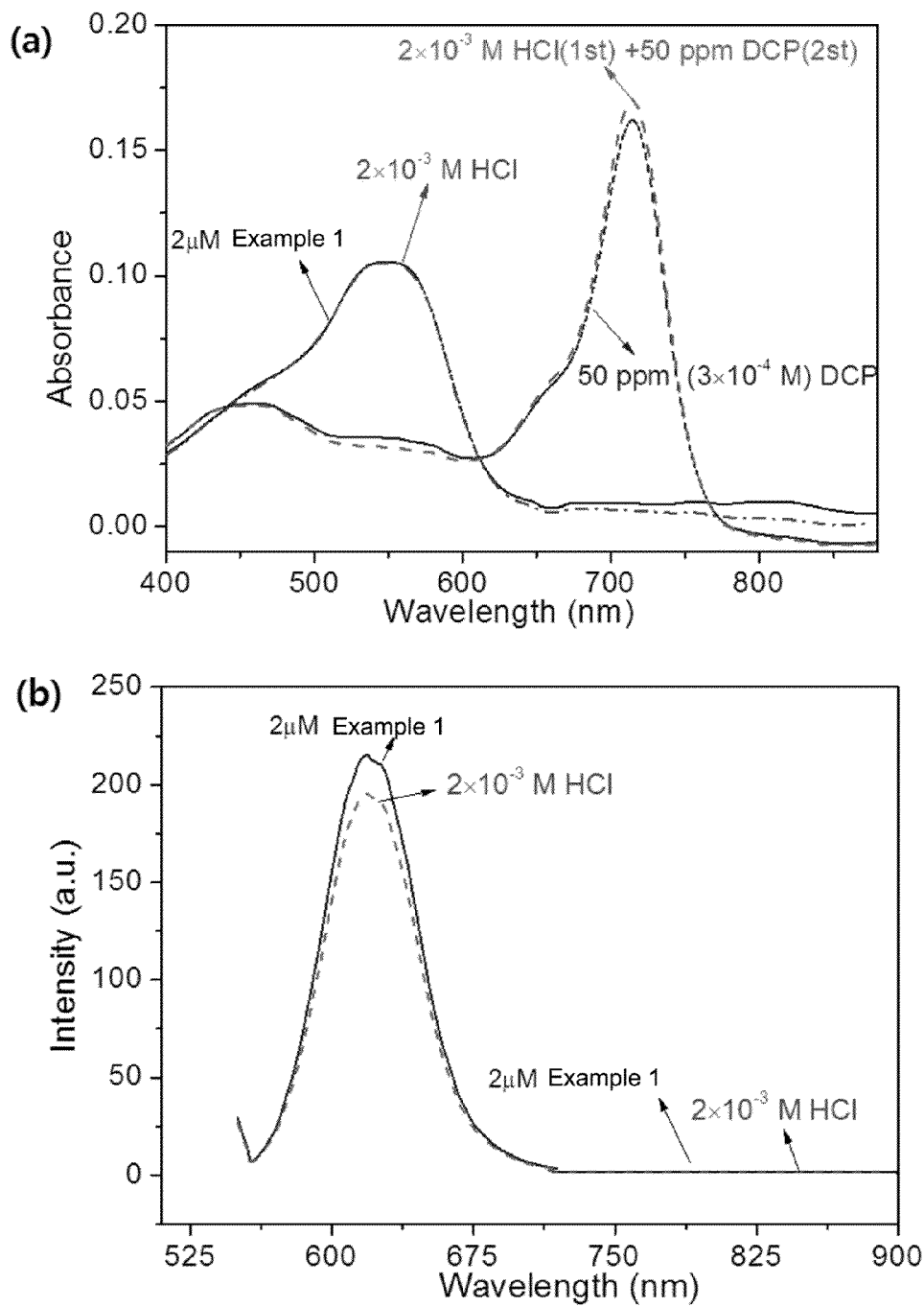
FIG. 8 are graphs showing absorbance spectra (a) and luminescence spectra (b) occurring when compound 1a according to an embodiment of the present invention reacts with a nerve poison gas analog DCP in a solvent of an aqueous condition.

FIG. 8 are graphs showing absorbance spectra (a) and luminescence spectra (b) occurring when compound 1a according to an embodiment of the present invention reacts with a nerve poison gas analog DCP in a solvent of an aqueous condition.

As shown in FIG. 8, when hydrochloric acid was added, a significant change was not observed in the absorbance/luminescence spectra. Meanwhile, when DCP was added, a significant change was observed in the absorbance spectra.

Thus, the cyanine derivative according to the present invention does not respond to a partial pH change generated when reacted with an organic phosphorous-based nerve agent in aqueous condition, but sensitively responds to DCP.

Experimental Example 7

Evaluation of Reaction Rate

To check the reaction rate between compound 1a prepared in Example 1 and an organic phosphorous-based nerve agent analog DCP, an experiment was performed as follows.

Specifically, compound 1a (2 μM) and DCP (0, 40, 60, 80, 100 ppm) were added in a mixture solution of $CH_3OH/H_2O$ (volume ratio: 80/20) and HEPES buffer (10 mM, pH=7.4) in aqueous condition as in Experimental Example 6, and absorbance/luminescence spectra of the generated compounds were measured using the absorbance/luminescence spectrometer used in Experimental Example 2, and the ratio of absorbance intensities ($A_{715\,nm}/A_{550nm}$) and the ratio of luminescence intensities ($I_{710nm\,ex}/I_{550\,nm\,ex}$) were calculated. Measurement results are shown in FIG. 9.

Figure 9:
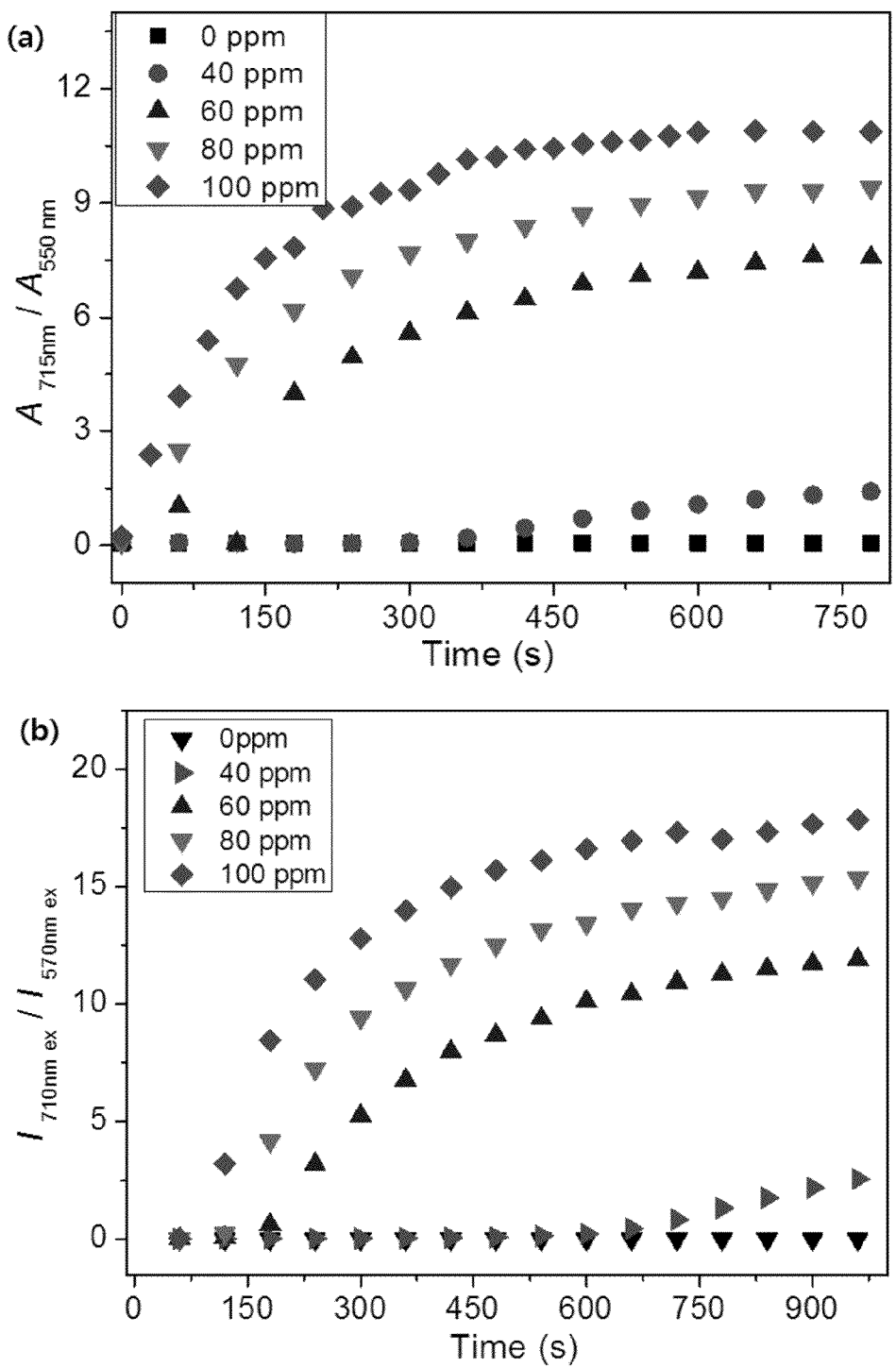
FIG. 9 are graphs showing reaction rates of compound 1a according to an embodiment of the present invention and a nerve poison gas analog DCP (FIG. 9 (a) is a graph showing a ratio ($A_{715\ nm}/A_{550\ nm}$) of absorbance as a function of concentration of DCP and time, and FIG. 9 (b) is a graph showing a ratio ($I_{710\ nm\ ex}/I_{550\ nm\ ex}$) of luminescence intensities as a function of concentration and time of DCP).

FIG. 9 are graphs showing reaction rates of compound 1a according to an embodiment of the present invention and a nerve poison gas analog DCP (FIG. 9 (a) is a graph showing a ratio ($A_{715\,nm}/A_{550nm}$) of absorbance as a function of concentration of DCP and time, and FIG. 9 (b) is a graph showing a ratio ($I_{710\,nm\,ex}/I_{550\,nm\,ex}$) of luminescence intensities as a function of concentration and time of DCP).

As shown in FIG. 9, it was confirmed that the higher the concentration of DCP was, the higher the ratios of the absorbance intensities and luminescence intensities were. Based on these results, pseudo first-order rate constant (k) was calculated to obtain k of about 0.2 $min^{-1}$.

Thus, the cyanine derivative according to the present invention exhibit a remarkably fast detection rate of DCP in aqueous solution, compared with that according to the related art method.

Experimental Example 8

Manufacturing of Film for Detection of Nerve Agent and Evaluation of Detection

A film practically applicable film for detection of a nerve agent was manufactured using compound 1a prepared in Example 1.

Specifically, a mixture solution of compound 1a and methanol was added dropwise on a quartz plate and then spread to manufacture a thin film. After the manufactured film was put in a sealing container filled with inert argon gas, DCP gas (10 ppm) was injected, and observation was performed under a 365 nm UV lamp. Measurement results are shown in FIG. 10.

Figure 10:
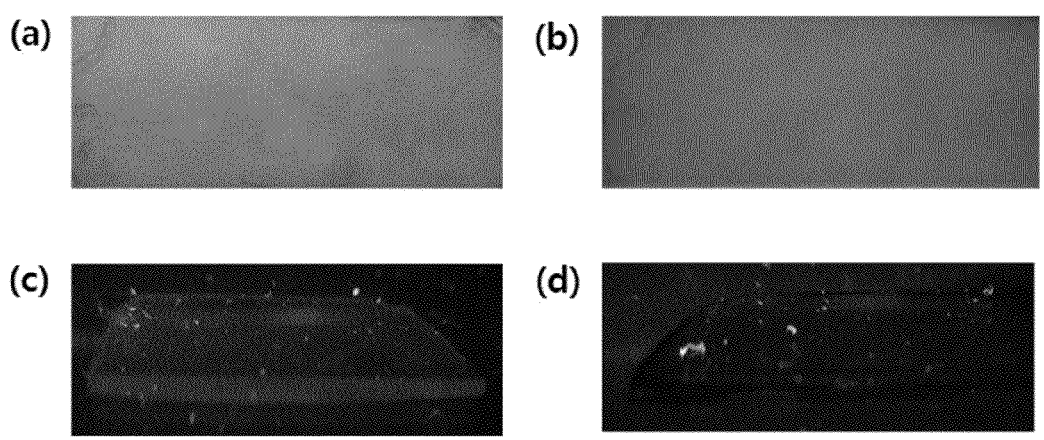
FIG. 10 is photographs showing a change in color before and after detection of a nerve poison gas analog DCP by using a film coated with compound 1a according to an embodiment of the present invention.

FIG. 10 is photographs showing a change in color before and after detection of a nerve poison gas analog DCP by using a film coated with compound 1a according to an embodiment of the present invention.

As shown in FIG. 10, it was confirmed that the film before being exposed to DCP gas was red, whereas the film after being exposed to DCP gas was very rapidly (almost immediately) changed to green.

Thus, the cyanine derivative according to the present invention can be manufactured into a simple solid sensor for detecting an organic phosphorous-based nerve agent and has a very fast reaction rate.

The invention claimed is:

1. A novel cyanine derivative having a meso-reaction functional group at a polymethine chain expressed by the following formula 1:

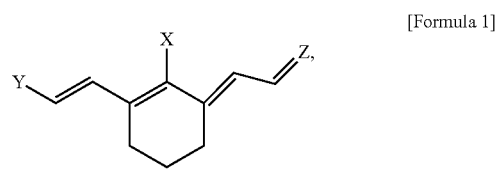

[Formula 1]

where X is —$NH_2$, —NCO, —NCS, —$N_3$,

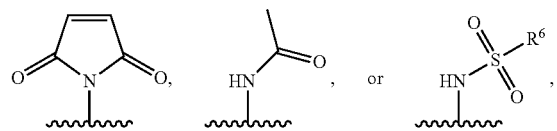

Y is

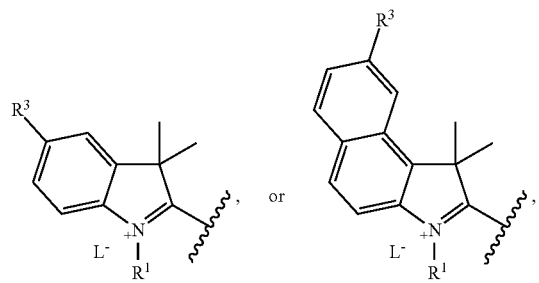

Z is

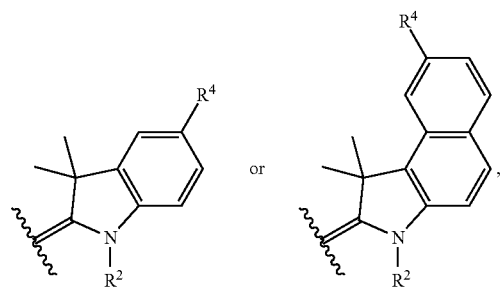

L⁻ is Cl⁻, Br⁻, I⁻, ClO₄⁻ or PF₆⁻,

R¹ and R² are independently —(CH₂)ₙR⁷, —(CH₂)ₘOR⁸, —(CHR⁹CH₂O)ₚR⁸ or

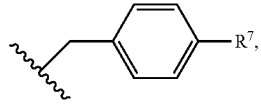

R³, R⁴ and R⁷ are independently —H, —SO₃R¹⁰ or —CO₂R¹¹,

R⁵ is

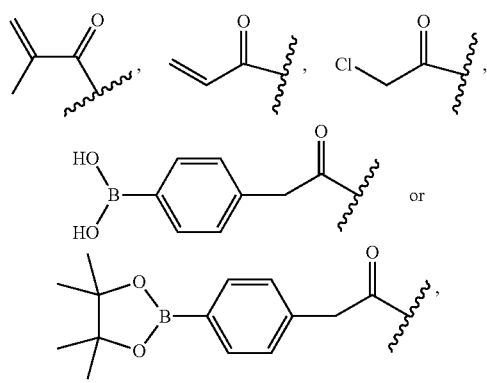

R⁶ is

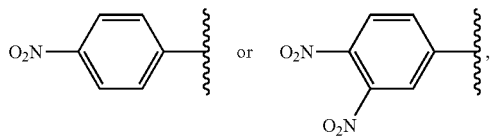 [SMILES: *c1ccc([N+](=O)[O-])cc1 ; *c1ccc([N+](=O)[O-])c([N+](=O)[O-])c1]

R⁸ is —H or —(CH₂)_qCH₃,
R⁹ is —H or —CH₃,
R¹⁰ is —H or -M,
R¹¹ is —H, -M or —(CH₂)_qCH₃,
M is Na, K or —N(R⁸)₄,
m, p and q are independent integers ranging from 0 to 18, and
n is integers ranging from 0-4 and 6-18.

2. The cyanine derivative as set forth in claim 1, where X is —NH₂, —NCO, —NCS, or —N₃,
Y is

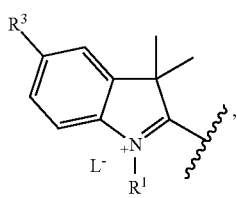

Z is

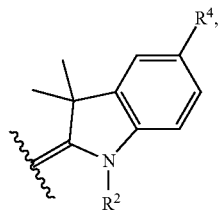

L⁻ is Cl⁻, Br⁻, or I⁻,
R¹ and R² are independently —(CH₂)ₙR⁷, —(CH₂)ₘOR⁸, or (CHR⁹CH₂O)ₚR⁸,
R³, R⁴ and R⁷ are independently —H, or —CO₂R¹¹,
R⁵ is

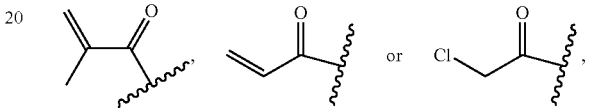

R⁶ is

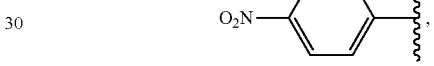

R⁸ is —H or —(CH₂)_qCH₃,
R⁹ is —H or —CH₃,
R¹⁰ is —H or -M,
R¹¹ is —H or -M,
M is Na or K,
m, p and q are independent integers ranging from 0 to 10, and
n is integers ranging from 0-4 and 6-10.

3. The cyanine derivative as set forth in claim 1, where X is —NH₂, or —NCO,
Y is

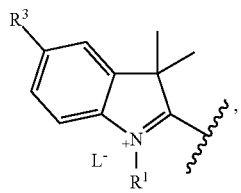

Z is

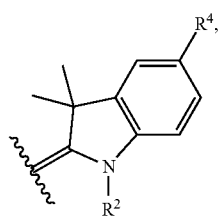

L⁻ is Cl⁻, Br⁻ or I⁻,
R¹ and R² are independently C₁₋₃ straight chain alkyl,
R³ and R⁴ are independently —H or —CO₂H.

4. The cyanine derivative as set forth in claim 1, wherein
X is —NH$_2$,
Y is

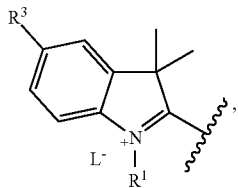

Z is

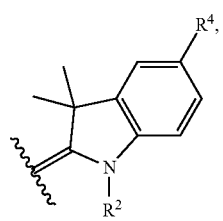

L$^-$ is I$^-$,
R$^1$ and R$^2$ are —CH$_3$, and
R$^3$ and R$^4$ are —H.

5. A method of preparing a cyanine derivative, as described in the following reaction formula 1, the method comprising:
reacting compound 3 and phthalimide potassium in a first solvent to obtain compound 2 in which the phthalimide is substituted for a meso site of compound 3 (step 1); and
reacting compound 2 prepared in step 1 and X—NH$_2$ in a second solvent to obtain compound 1 in which X is substituted for a meso site of compound 2 (step 2):

[Reaction formula 1]

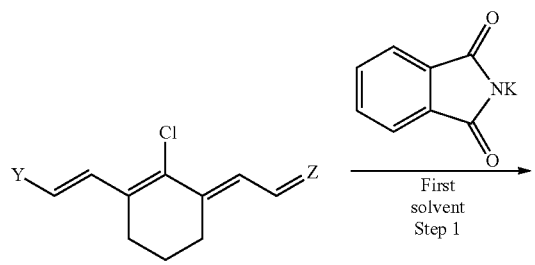

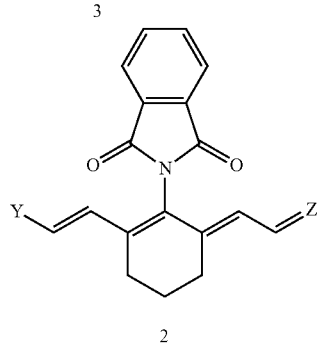

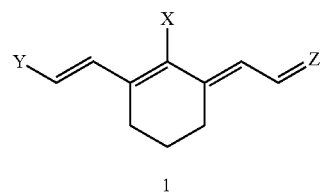

1 where X, Y and Z are those defined in formula 1 of claim 1.

6. The method of preparing a cyanine derivative as set forth in claim 5, wherein the first solvent is one selected from the group consisting of dimethylformamide, dimethylacetamide, dimethylether, tetrahydrofuran, 1,4-dioxane, benzene, and toluene.

7. The method of preparing a cyanine derivative as set forth in claim 5, wherein the second solvent is one selected from the group consisting of methanol, ethanol, propanol, and butanol.

8. A ratiometric chemsensor for detection of pH, comprising a cyanine derivative expressed by the following formula 1:

[Formula 1]

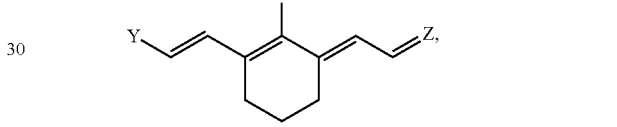

where X is —NH$_2$,
Y is

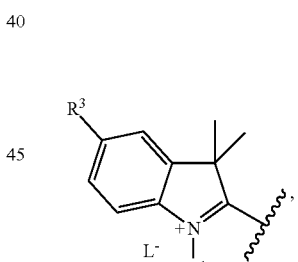 or 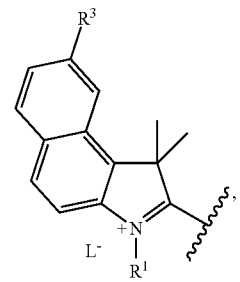

Z is

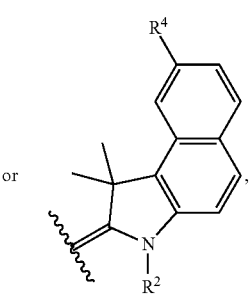

$L^-$ is $Cl^-$, $Br^-$, $I^-$, $ClO_4^-$ or $PF_6^-$, $R^1$ and $R^2$ are independently $-(CH_2)_nR^7$, $-(CH_2)_mOR^8$, $-(CHR^9CH_2O)_pR^8$ or

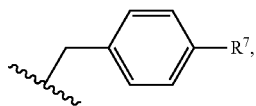

$R^3$, $R^4$ and $R^7$ are independently $-H$, $-SO_3R^{10}$ or $-CO_2R^{11}$, $R^5$ is

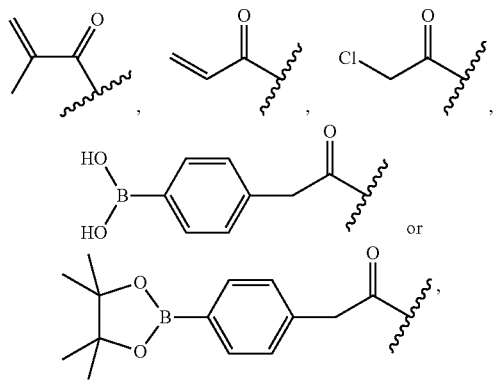

$R^6$ is

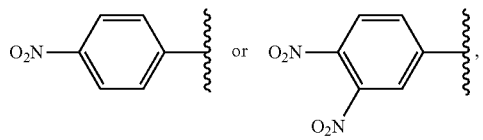

$R^8$ is $-H$ or $-(CH_2)_qCH_3$, $R^9$ is $-H$ or $-CH_3$, $R^{10}$ is $-H$ or $-M$, $R^{11}$ is $-H$, $-M$ or $-(CH_2)_qCH_3$,

M is Na, K or $-N(R^8)_4$, and m, p and q are independent integers ranging from 0 to 18, and n is integers ranging from 0-4 and 6-18.

9. The ratiometric chemosensor for detection of pH as set forth in claim 8, wherein the chemosensor is applied to paper, film or a particle-shaped substrate.

10. A method of detecting pH change using ratiometric mode with the cyanine derivative expressed by formula 1 of claim 8.

11. The method as set forth in claim 10, characterized by measuring absorbance or luminescence characteristic caused by a change of a n-conjugation system occurring when proton is added to a meso-reaction functional group of a polymethine chain of the cyanine derivative expressed by formula 1.

12. A chemsensor for detection of an organic phosphorous-based nerve agent, the chemosensor comprising a cyanine derivative expressed by formula 1 as set forth in claim 1.

13. The chemosensor as set forth in claim 12, wherein the chemosensor is applied to paper, film or a particle-shaped substrate.

14. A method of detecting an organic phosphorous-based nerve agent using a cyanine derivative expressed by formula 1 of claim 1.

15. The method as set forth in claim 14, wherein the method of detecting an organic phosphorous-based nerve agent is characterized by measuring changes of decoloration, extinction and eradiation characteristics solely or in combination, caused by a change of a π-conjugation system occurring when a meso-reaction functional group of a polymethine chain of the cyanine derivative expressed by formula 1 undergoes a substitution reaction with an organic phosphorous-based nerve agent.

* * * * *

UNITED STATES PATENT AND TRADEMARK OFFICE
CERTIFICATE OF CORRECTION

PATENT NO. : 9,151,735 B2  
APPLICATION NO. : 13/813764  
DATED : October 6, 2015  
INVENTOR(S) : Juyoung Yoon et al.

Page 1 of 1

It is certified that error appears in the above-identified patent and that said Letters Patent is hereby corrected as shown below:

In the Claims

Column 18, claim 1, line 30, 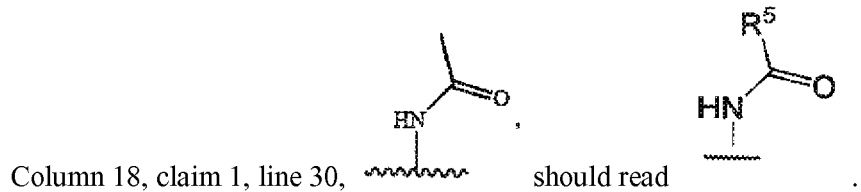 should read .

Signed and Sealed this  
Eighth Day of March, 2016

Michelle K. Lee  
*Director of the United States Patent and Trademark Office*